US010531665B2

(12) United States Patent
Schepers et al.

(10) Patent No.: US 10,531,665 B2
(45) Date of Patent: Jan. 14, 2020

(54) HETEROPOLYOXOMETALATES

(71) Applicant: POM Patentverwaltungs GbR, Braunfels (DE)

(72) Inventors: Klaus Schepers, Braunfels (DE); Horst Mischo, Trier (DE); Pierre-Alain Weiss, Schwalbach (DE); Ulrich Kortz, Bremen (DE); Bassem S. Bassil, Bremen (DE); Maria Barsukova-Stuckart, Bremen (DE); Rami Al-Oweini, Bremen (DE); Andreas Suchopar, Bremen (DE); Ali Haider, Bremen (DE); Alexander Birkel, Darmstadt (DE); Balamurugan Kandasamy, Bremen (DE)

(73) Assignee: POM Patentverwaltungs GbR, Braunfels (DE)

( * ) Notice: Subject to any disclaimer, the term of this patent is extended or adjusted under 35 U.S.C. 154(b) by 42 days.

(21) Appl. No.: 14/766,279

(22) PCT Filed: Feb. 6, 2014

(86) PCT No.: PCT/EP2014/052360
§ 371 (c)(1),
(2) Date: Aug. 6, 2015

(87) PCT Pub. No.: WO2014/122225
PCT Pub. Date: Aug. 14, 2014

(65) Prior Publication Data
US 2015/0373987 A1 Dec. 31, 2015
US 2017/0150725 A9 Jun. 1, 2017

(30) Foreign Application Priority Data

Feb. 6, 2013 (EP) .................................... 13154137
Apr. 17, 2013 (EP) .................................... 13164081
May 22, 2013 (EP) .................................... 13168791
Oct. 7, 2013 (EP) .................................... 13187567

(51) Int. Cl.

| | | |
|---|---|---|
| A01N 59/16 | (2006.01) |
| C07F 11/00 | (2006.01) |
| A61L 2/18 | (2006.01) |
| A61L 9/04 | (2006.01) |
| A61L 2/232 | (2006.01) |
| A61L 2/238 | (2006.01) |
| C09D 5/16 | (2006.01) |
| A47J 31/44 | (2006.01) |
| C09D 5/14 | (2006.01) |
| A61L 9/18 | (2006.01) |
| C02F 1/72 | (2006.01) |
| F24C 15/00 | (2006.01) |
| A47J 31/60 | (2006.01) |

(52) U.S. Cl.
CPC .............. *A01N 59/16* (2013.01); *A47J 31/44* (2013.01); *A61L 2/18* (2013.01); *A61L 2/232* (2013.01); *A61L 2/238* (2013.01); *A61L 9/04* (2013.01); *C07F 11/005* (2013.01); *C09D 5/14* (2013.01); *C09D 5/1625* (2013.01); *A47J 31/60* (2013.01); *A61L 9/18* (2013.01); *A61L 2202/11* (2013.01); *A61L 2202/23* (2013.01); *A61L 2209/21* (2013.01); *C02F 1/725* (2013.01); *C02F 2303/20* (2013.01); *F24C 15/005* (2013.01)

(58) Field of Classification Search
None
See application file for complete search history.

(56) References Cited

U.S. PATENT DOCUMENTS 5,066,740 A 11/1991 Rhodes

FOREIGN PATENT DOCUMENTS

| | | |
|---|---|---|
| CN | 1203231 A | 12/1998 |
| CN | 1092190 C | 10/2002 |
| CN | 101302147 A | 11/2008 |
| CN | 101768106 A1 | 7/2010 |
| CN | 101302147 B | 5/2011 |
| CN | 102295603 A | 12/2011 |
| EP | 0435146 A2 | 7/1991 |
| FI | 906404 A | 6/1991 |
| JP | 1993213918 A | 8/1993 |
| JP | 06220171 A | 8/1994 |
| JP | 2005161208 A | 6/2005 |
| JP | 2005281299 A | 10/2005 |
| JP | 2006257029 A | 9/2006 |
| JP | 2009214094 A | 9/2009 |
| JP | 20100257772 A | 11/2010 |
| JP | 5447791 B2 | 3/2014 |
| WO | 9217215 A1 | 10/1992 |
| WO | 2006110166 A2 | 10/2006 |

OTHER PUBLICATIONS

Ding et al. (Nanotechnolgy 16, 785-790, 2005)Polyoxometalate nanotubes from . . . .*
Selig, Walter, Constant-current potentiometric titration of orthophosphate with cetylpyridinium chloride: a feasability study, Talanta, Sep. 1983, pp. 695-698, vol. 30, Issue 9, Livermore, United States.
Ishii, Yasutaka et al., Hydrogen Peroxide Oxidation Catalyzed by Heteropoly Acids Combined with Cetylpyridinium Chloride: Epoxidation of Olefins and Allylic Alcohols, Ketonization of Alcohols and Diols, and Oxidative Cleaveage of 1,2-Diols and Olefins, The Journal of Organic Chemistry, Jul. 1988, pp. 3587-3593, vol. 53, Issue 15, Osaka, Japan.
Arcoria, Antonino et al., Kientics of mechanism of oxidation of organic sulfides and olefins by a molybdenum peroxopolyoxoanion, Gazzetta Chimica Italiana, 1990, pp. 309-313, vol. 120, Issue 5, Catania, Italy.

(Continued)

*Primary Examiner* — Tigabu Kassa
(74) *Attorney, Agent, or Firm* — Honigman LLP; James K. Leonard; Jonathan P. O'Brien

(57) ABSTRACT

The present invention relates to the use of heteropolyoxometalates for disinfecting purposes and in antimicrobial surfaces, paints or coatings and intermediates for their preparation.

12 Claims, 2 Drawing Sheets

(56) References Cited

OTHER PUBLICATIONS

Yu, Jian-Feng et al., Structure and Catalytic Activity for PhOH Hydroxylation with H2O2 of Dawson Molybdovanadophosphoric Compounds, Gaodeng Uxexiao Huaxue Xuebao, 1996, 1 page, vol. 17, Issue 1, Changchun, China.

Yang, Yu et al., The role and mechanism of tungstovanadophosphates in the hydroxylation of phenol with hydrogen peroxide, Ciuhua Xuebao, 1997, 4 pages, vol. 18, Issue 3, Changchun, China.

Maksimov, G.M. et al., Acidity of heteropoly acids with various structures and compositions studied by IR spectroscopy of the pyridinium salts, Russian Chemical Bulletin, Apr. 2001, pp. 587-590, vol. 50, Issue 4, Novosibirsk, Russia.

Chhikara, Bhupender S. et al., Oxidation of alcohols with hydrogen peroxide catalyzed by a new imidazolium ion based phosphotungstate complex in ionic liquid, Journal of Catalysis, Mar. 10, 2005, pp. 436-439, vol. 230, Issue 2, Delhi, India.

Wang, Kun et al., Preparation and electrocatalytic properties of inorganicorganic hybrid polyoxometalate [Bmim] 5 PMo10 V2 O40, Yingyong Hyaxue, 2009, 2 pages, vol. 26, Issue 1, Zhenjiang, China.

Ding, Yong et al., Synthesis of Expoxides Catalyzed by a Halide-Free Reaction-Controlled Phase-Transfer Catalytic System: [ (CH3 (CH2) 17) 2N (CH3) 2 ] 3 [PW4O32] / H2O2/Dioxan/Olefin, Australian Journal of Chemistry, Jul. 13, 2009, pp. 739-749, vol. 62, Issue 7, Lanzhou, China.

Cai, Tie-Jun et al., Crystal structure and catalytic properties of (C6H8N) 3 [PMo12O40], Zeitschrift fuer Naturforschung (A Journal of Chemical Sciences), 2011, pp. 1231-1236, vol. 66, Issue 12, Xiangtan, China.

Leng, Yan et al., Heteropolyanion-based ionic hybrid solid: A green bulk-type catalyst for hydroxylation of benzene with hydrogen peroxide, Chemical Engineering Journal, 2011, pp. 620-626, vol. 173, Issue 2, Changshu, China.

Wang, Ruiying et al., Facile synthesis and enhanced electrocatalytic activiteis of organic-inorganic hybrid ionic liquid polyoxometalate nanomaterials by solid-state chemical reaction, Electrochimica Acta, 2012, pp. 101-107, vol. 72, Xinjiang, China.

Zhao, Pingping et al., Heterogeneous Selective Oxidation of Sulfides with H2O2 Catalyzed by Ionic Liquid-Based Polyoxometalate Salts, Industrial Chemistry Research, Apr. 25, 2012, pp. 6641-6647, vol. 51, Issue 19, Nanjing, China.

International Searching Authority, International Search Report and Written Opinion for International Application No. PCT/EP2014/052360, 17 pages, dated May 14, 2014.

\* cited by examiner

HETEROPOLYOXOMETALATES

BACKGROUND OF THE INVENTION

The present invention relates to the use of heteropolyoxometalates for disinfecting purposes and in antimicrobial surfaces, paints or coatings and intermediates for their preparation.

In many industrial and domestic processes waste water is produced or fresh water is to be stored for later purposes. As essentially all water sources provide non-sterile water, in fresh water and in particular in waste water there is the risk of microbiological contamination during storage or processing.

Many ways are known in the art to avoid creation of microbiological contaminations, in particular biofilms, in containers for the storage of drinking water, waste water, surface water or similar liquids. Further, several methods are known to avoid microbiological contamination of surfaces, e.g. in hospitals or slaughterhouses. For example, usually the surfaces of containers are cleaned by heat treatment, e.g. by rinsing the surfaces or containers with hot liquids or gases, e.g. hot water or steam. Further, treatment by ozone or chlorine containing gases is known for disinfecting surfaces and containers and cleaning and removal of organic contaminations.

It is also known to apply ultraviolet (UV-) radiation to disinfect surfaces, containers, and even liquids. It is also known to add certain substances to the liquids, such as titanium dioxide, or to apply titanium dioxide to a surface for disinfecting or cleaning purposes. However, these surfaces and substances require UV-radiation for activating the disinfecting efficacy of titanium dioxide.

Further, it is known to apply silver ions or copper ions to solutions in order to reduce the microbiological contamination.

All these measures and procedures are disadvantageous as they waste a lot of energy, require high apparatus cost and costs of operation in order to be sufficiently effective, or rather expensive substances, such as silver ions or copper ions, have to be used, the latter having further disadvantages with regard to water and soil pollution. Further, using substances which are dangerous to handle, e.g. ozone or chlorine containing substances, as well as ultraviolet radiation, is disadvantageous and requires additional safety measures.

The use of polyoxometalates is known in the art for several purposes, e.g. in the general area of analytical chemistry (e.g. elemental analysis, electron staining), the use as catalysts including photo catalysts, in biochemistry for inhibiting electron transfer processes and as electron-dense and rigid components in the crystallization of biomolecules (e.g. ribosomes, leading to the 2009 Nobel Prize), and in medicine due to their antiviral and antitumor activity. The use of polyoxometalates as acid and oxidation catalysts is known in industry (e.g. for the hydration of olefins).

There is still a need in the art to provide an effective, environmentally friendly and cheap measurement to avoid microbial contamination of liquids and surfaces.

DETAILED DESCRIPTION

Figure 1:
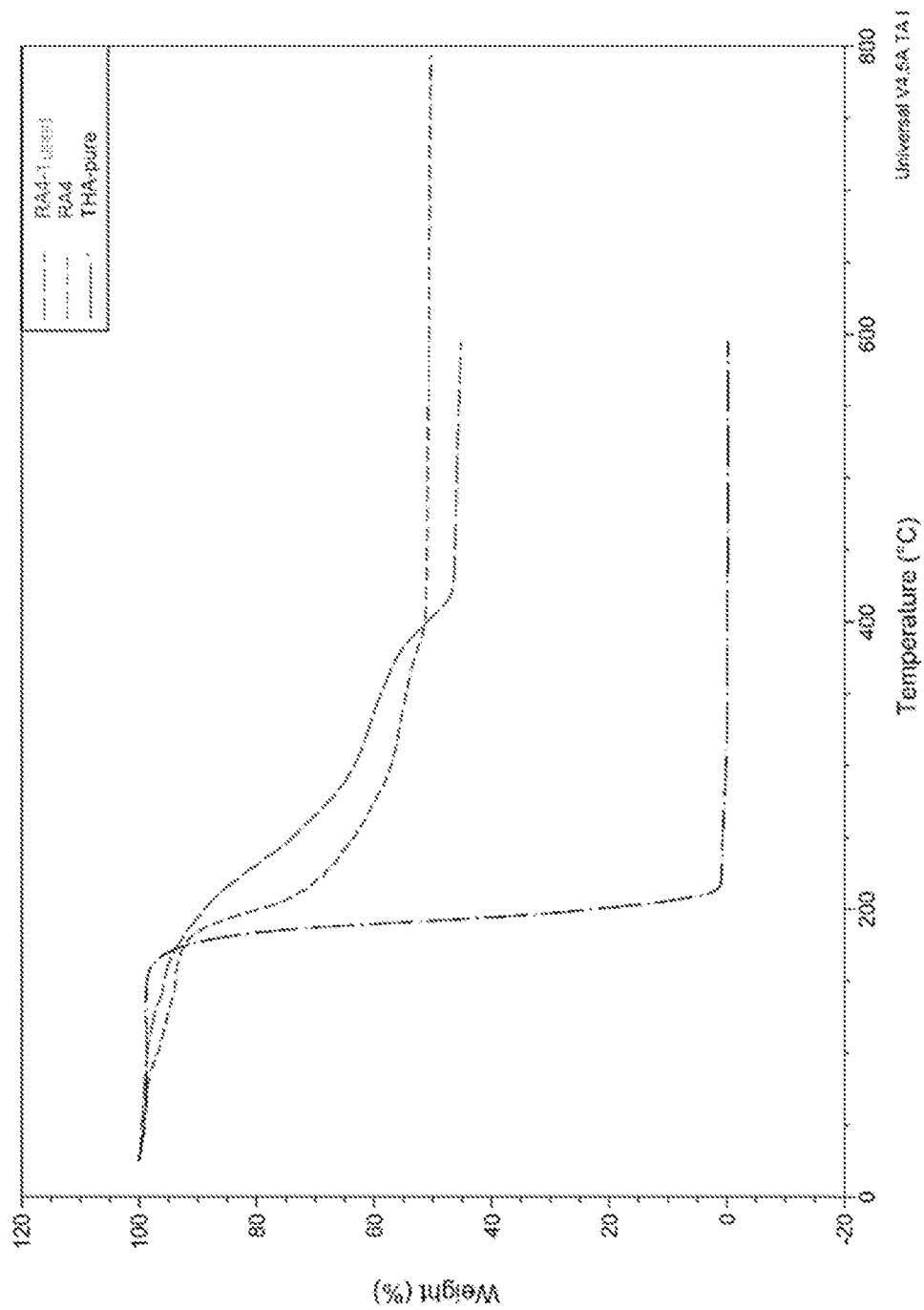
FIG. 1 shows the TGA/DSC measurement results of the heteropolyoxometalate of Example 3.

It has been surprisingly found that certain heteropolyoxometalates provide excellent antimicrobial efficiency when applied to surfaces, which are in contact with liquids, in particular with waste water, and thereby avoid microbiological contamination of surfaces and of the liquid and lead to a reduction of biofilm formation.

In particular, it has been found that certain heteropolyoxometalates based on phosphorous in combination with molybdenum or tungsten and at least one quaternary ammonium or phosphonium cation or at least one tertiary sulfonium cation as defined below show excellent antimicrobial activity, compared to other heteropolyoxometalates, in particular the known heteropolyoxometalates based on silicon. Surprisingly, the antimicrobial activity seems to be assured by the simple presence of oxygen in the air or dissolved in liquids, thus no activation of the heteropolyoxometalate is necessary, and no addition of activation agents.

Therefore, the present invention relates to the use of heteropolyoxometalates of the Formula (I), (II) or (III):

$$A_{q+3}PV_qZ_{12-q}O_{40} \quad (I)$$

$$A_6P_2Z_{18}O_{62} \quad (II), or$$

$$A_3PZ_4O_{24} \quad (III)$$

wherein
Z is selected from Mo or W,
index q=0, 1, 2 or 3, and
A is selected from one or more cations and comprises at least one cation selected from the group consisting of quaternary ammonium cations, quaternary phosphonium cations and tertiary sulfonium cations for providing self-cleaning, stripping, disinfecting, self-sanitizing, biocidal, antimicrobial, and/or deodorizing properties to at least part of a substrate or a surface of a substrate or to a coating or for decomposition and/or degradation of organic materials.

It is understood that, if due to the selection of the cation A in the heteropolyoxometalate the charge of the compound of the Formula (I), (II) or (III) should not be zero, then either the number of cations A can be reduced and/or the charge is balanced by one or more further cations and/or anions.

The present invention also relates to the use of a mixture of two or more differing heteropolyoxometalates of formula (I), (II) or (III), i.e. at least one parameter Z or q is selected differently for each anion of each cation A, or the same heteropolyoxometalate anion of formula (I), (II) or (III) is present together with at least two differing cations A.

The present invention in a certain embodiment also relates to the use of a mixture of several differing heteropolyoxometalates of formula (I), (II) or (III), i.e. at least one parameter Z or q is selected differently for each anion of each quaternary ammonium cation A, or the same heteropolyoxometalate anion of formula (I), (II) or (III) is present together with at least two differing quaternary ammonium cations.

Generally, polyoxometalates based on molybdenum (Mo) or tungsten (W) are known in the art, in particular as Keggin-type polyanions $[XZ_{12}O_{40}]^{n-}$, wherein X is selected from P, Si, Ge, As, B or Al. It is also known that the Keggin-type polyoxometalates contain a central heteroatom (X), which can be e.g. phosphorus ($P^{5+}$), silicon ($Si^{4+}$), germanium ($Ge^{4+}$), etc. Further, in the Keggin-type polyoxometalate based on molybdenum or tungsten one or more, in particular 1 to 3, molybdenum or tungsten atoms may be replaced by vanadium atoms (e.g. $V^{5+}$). Another example of polyoxoanions is the Wells-Dawson species $[X_2Z_{18}O_{62}]^{n-}$. This polyanion contains two heteroatoms (X), which can be phosphorus ($P^{5+}$) or arsenic ($As^{5+}$) and 18 molybdenum or tungsten atoms (Z). Further, in the Wells-Dawson-type polyoxometalate based on tungsten one or more, in particular 1 to 3, tungsten atoms may be replaced by vanadium atoms (e.g. $V^{5+}$). Also several types of peroxotungstates are known. One of the most important ones is the Venturello polyoxoanion $[PW_4O_{24}]^{3-}$, whose catalytic properties have been widely studied. The Venturello polyoxoanion consists of the central $[PO_4]^{3-}$ group, which is connected to four $\{WO(O_2)_2\}$ units. Generally, these polyoxometalate anions are known in the art, and the negative charge of the known anions is typically counterbalanced by cations like $Li^+$, $Na^+$, $K^+$ or $NH_4^+$ which provide solubility of the resulting salts in water.

The heteropolyoxometalates used in the present invention, on the other hand, were found to be less soluble or even insoluble in water. Thus, it was found that when A is selected as described above to counterbalance the negative charge of the certain heteropolyoxometalates, the heteropolyoxometalates, as a result, are rendered less soluble or even insoluble in water.

It was also surprisingly found that when A is selected as described above to counterbalance the charge of the heteropolyoxometalates, then the heteropolyoxometalates, as a result, are not only less soluble or even insoluble in water but also possess favorable stability, specifically thermal stability, in particular when the said cations are quaternary phosphonium cations. This thermal stability can be very advantageous, especially when the heteropolyoxometalates are included in such substrates as tiles, ceramics, enamels, glazes, coatings, or other materials that require high temperatures e.g. for firing and/or finishing.

In the heteropolyoxometalates used according to the present invention A is selected from one or more cations and comprises at least one cation selected from the group consisting of quaternary ammonium cations, quaternary phosphonium cations and tertiary sulfonium cations. These cations are used to counterbalance the negative charge of the heteropolyoxometalate anions. It is preferred that, more than one, more than two, or, if applicable, more than three, more than four, or even all cations are selected from the list above. If more than one cation is selected from the list, these may be the same or different.

In the heteropolyoxometalates used in the present invention the "heteroatom" is phosphorous. Preferred are the heteropolymolybdate derivatives of the fomula (I), wherein residue Z is molybdenum (Mo), and polytungstates of formula (III), wherein residue Z is tungsten (W).

In a preferred embodiment in the heteropolyoxometalate of formula (I) index q is 2 or 3, in particular 2. This means that in the heteropolyoxometalate based on molybdenum or tungsten, from the 12 molybdenum oxide or tungsten oxide subunits two or three are replaced by vanadium oxide subunits. In an especially preferred embodiment, the heteropolyoxometalate is of the formula (VII).

$$A_5PV_2Z_{10}O_{40} \tag{VII}$$

wherein Z is selected from Mo or W; A is selected from one or more cations and comprises at least one quaternary ammonium cation, quaternary phosphonium cation or tertiary sulfonium cation, the quaternary ammonium and phosphonium cation being preferred. Another preferred example is $A_5PMo_{10}V_2O_{40}$.

In another specifically preferred embodiment in the heteropolyoxometalate of formula (III) residue Z is W, i.e. the heteropolyoxometalate is $A_3PW_4O_{24}$.

In the heteropolyoxometalates used in the present invention, A is selected from one or more cations. The quaternary ammonium cation can be of Formula (IV), the quaternary phosphonium cation can be of Formula (V) and the tertiary sulfonium cation can be of Formula (VI)

$$R^1R^2R^3R^4N^+ \tag{IV}$$

$$R^1R^2R^3R^4P^+ \tag{V}$$

$$R^1R^2R^3S^+ \tag{VI}$$

wherein residues $R^1$, $R^2$, $R^3$ and $R^4$ can be independently selected. Preferably, residues $R^1$, $R^2$, $R^3$ and $R^4$ are independently selected from hydrocarbons including polymers. Preferably the hydrocarbons are $C_1$ to $C_{20}$ hydrocarbons, more preferably $C_1$ to $C_{16}$ hydrocarbons, in particular $C_2$ to $C_8$ hydrocarbons, e.g. $C_4$ to $C_6$ hydrocarbons or $C_4$ to $C_{16}$ hydrocarbons. The hydrocarbons being preferably branched or straight, saturated or unsaturated alkyl groups, aryl groups or heteroaryl groups. Examples are methyl, ethyl, propyl, butyl, pentyl, hexyl, heptyl, octyl, nonyl, decyl, undecyl, dodecyl, tridecyl, tetradecyl, pentadecyl, hexadecyl, heptadecy and octadecyl residues. Optionally, two of the residues $R^1$, $R^2$, $R^3$ and, if present, $R^4$ are part of a ring, e.g. together form a ring, optionally together with the central nitrogen, phosphor or sulfur atom. The ring may be saturated or unsaturated, such as aromatic.

Specifically preferred quaternary ammonium cations are tetrapropylammonium cation, tetrabutylammonium cation, tetrapentylammonium cation, tetrahexylammonium cation, tetraheptylammonium cation, tetraoctylammonium cation, tetranonylammonium cation, tetradecylammonium cation, tetraundecylammonium cation, tetradodecylammonium cation, tetratridecylammonium cation, tetratetradecylammonium cation, tetrapentadecylammonium cation, methyltributylammonium cation, methyltripentylammonium cation, methyltrihexylammonium cation, methyltriheptylammonium cation, methyltrioctylammonium cation, methyltrinonylammonium cation, methyltridecylammonium cation, methyltriundecylammonium cation, methyltridodecylammonium cation, methyltritridecylammonium cation, methyltritetradecylammonium cation, tributylhexylammonium cation, tributylheptylammonium cation, tributyloctylammonium cation, tributylnonylammonium cation, tributyldecylammonium cation, tributylundecylammonium cation, tributyldodecylammonium cation, tributyltridecylammonium cation, tributyltetradecylammonium cation, tributylpentadecylammonium cation, tributylhexadecylammonium cation, trihexyltetradecylammonium cation and trihexylhexadecylammonium cation, in particular tetrabutylammonium cation, tetrahexylammonium cation, methyltrioctylammonium cation, tributyltetradecylammonium cation; specifically preferred quaternary phosphonium cations are tetrapropylphosphonium cation, tetrabutylphosphonium cation, tetrapentylphosphonium cation, tetrahexylphosphonium cation, tetraheptylphosphonium cation, tetraoctylphosphonium cation, tetraoctylphosphonium cation, tetranonylphosphonium cation, tetradecylphosphonium cation, tetraundecylphosphonium cation, tetradodecylphosphonium cation, tetratridecylphospphonium cation, tetratetradecylphosphonium cation, methyltrioctylphosphonium cation, tributyltetradecylphosphonium cation, tributyldodecylphosphonium cation, trihexyltetradecylphosphonium cation, trihexylhexadecylphosphonium cation in particular tetrabutylphosphonium cation, tetrahexylphosphonium cation, methyltributylphosphonium cation, methyltripentylphosphonium cation, methyltrihexylphosphonium cation, methyltriheptylphosphonium cation, methyltrioctylphosphonium cation, methyltrinonylphosphonium cation, methyltridecylphosphonium cation, tributylpentylphosphonium cation, tributylhexylphosphonium cation, tributylheptylphosphonium cation, tributyloctylphosphonium cation, tributylnonylphosphonium cation, tributyldecylphosphonium cation, tributylundecylphosphonium cation, tributyldodecylphosphonium cation, tributyltridecylphosphonium cation, tributyltetradecylphosphonium cation, tributylpentadecylphosphonium cation, tributylhexadecylphosphonium cation, trihexylheptylphosphonium cation, trihexyloctylphosphonium cation, trihexylnonylphosphonium cation, trihexyldecylphosphonium cation, trihexylundecylphosphonium cation, trihexyldodecylphosphonium cation, trihexyltridecylphosphonium cation, trihexyltetradecylphosphonium cation, trihexylpentadecylphosphonium cation and trihexylhexadecylphosphonium cation. Specifically preferred tertiary sulfonium cations are tripropylsulfonium cation, tributylsulfonium cation, tripentylsulfonium cation, trihexylsulfonium cation, triheptylsulfonium cation, trioctylsulfonium cation, methyldioctylsulfonium cation and dibutyltetradecylsulfonium cation, in particular tributylsulfonium cation and trihexylsulfonium cation. Further suitable ammonium, phosphonium and sulfonium cations and the preparation thereof are known in the art. Particularly preferred heteropolyoxometalates are e.g. $[(CH_3(CH_2)_3)_4N]_5$ $[PV_2Mo_{10}O_{40}]$, $[(CH_3(CH_2)_3)_4N]_3[PW_4O_{24}]$, $[(CH_3(CH_2)_5)_4N]_3[PW_4O_{24}]$, $[(CH_3(CH_2)_7)_4N]_3[PW_4O_{24}]$, $[(CH_3(CH_2)_7)_3N(CH_3)]_3[PW_4O_{24}]$ and $[(CH_3(CH_2)_3)_3P((CH_2)_{13}CH_3)]_3[PW_4O_{24}]$.

It furthermore was found that, if the cation A in the heteropolyoxometalates described above contains a polymer residue or a heterocyclic residue, the obtained heteropolyoxometalate exhibits particularly preferred properties with respect to low water solubility and thermal stability as well as high antimicrobial effectivity. The invention therefore also relates to heteropolyoxometalates of the formula $(I^H)$, $(II^H)$ or $(III^H)$ as well as the use of these heteropolyoxometalates for providing self-cleaning, stripping, disinfecting, self-sanitizing, biocidical, antimicrobial, and/or deodorizing properties to at least part of a substrate or a surface of a substrate or to a coating or for decomposition and/or degradation or organic materials $$A'_{q+3}PV_qZ_{12-q}O_{40} \quad (I^H),$$

$$A'_6P_2Z_{18}O_{62} \quad (II^H), \text{ or}$$

$$A'_3PZ_4O_{24} \quad (III^H)$$

wherein
Z is selected from Mo or W,
index q=0, 1, 2 or 3, and
A' is selected from one or more cations and comprises at least one cation selected from $$R^1R^2R^3R^4N^+ \quad (IV),$$

$$R^1R^2R^3R^4P^+ \quad (V),$$

$$R^1R^2R^3S^+ \quad (VI)$$

wherein residues $R^1$, $R^2$, $R^3$ and $R^4$ are independently selected from polymers and $C_1$ to $C_{20}$ hydrocarbons, and, if none of $R^1$, $R^2$, $R^3$ and $R^4$ is polymer, at least two of $R^1$, $R^2$, $R^3$ and, if present, $R^4$ form a ring together with the nitrogen, phosphor or sulfur atom.

The ring formed together with the nitrogen, phosphor or sulfur atom may, for example, be a three, four, five, six or seven-membered ring which may be saturated or unsaturated and which may contain one or more further heteroatoms, such as oxygen, nitrogen, phosphor or sulfur atoms. If the ring is unsaturated and if a double bond is present at the nitrogen, phosphor or sulfur atom of the ammonium, phosphonium or sulfonium cation, then one of $R^1$, $R^2$ $R^3$ or $R^4$ may be absent. Examples of suitable rings are aziridinium, thiiranium, azetidinium, thietium, pyrrolidinium, tetrahydrothiophenium, pyrrolium, thiophenium, piperidinium, tetrahydrothiopyranium, pyridinium, thiopyrylium, hexamethyleniminium, hexamethylensulfidium, azatropilidenium, thiotropilidenium, pyrazolium, imidazolium, benimidazolium, imidazolinium, indolium, chinolinium, isochinolinium, purinium, pyrimidinium, oxazolium, thiazolium and thiazinium as well as the phosphorous analogs of these ring systems.

The rings may be substituted by one or more hydrocarbon residues, in particular $C_1$ to $C_{12}$ alkyl or aryl (in particular phenyl) $C_1$ to $C_6$ alkyl residues. Suitable cations containing a ring are for example 1-butyl-3-methylimidazolium, 1-butyl-2,3-dimethylimidazolium, 1-methyl-3-octylimidazolium, 1-hexadecyl-3-methylimidazolium, 1,3-didecyl-3-methylimidazolium and 1-benzyl-3-methylimidazolium.

Suitable polymers are for example polymers comprising cationic side chains, such as phosphonium-containing cationic poly(styrene) polymers, hydroxy exchange membranes comprising quaternary ammonium hydroxide or quaternary phosphonium hydroxide functional groups, poly (vinylamine) derivatives as described for example in EP 0 580 078 A1, polymeric phosphonium ionomers, as described for example in WO 94/10214, poly(alkyl- and aryl)p-phenoxy-phenylsulfonium salts, poly(acrylamide-co-diallyl-dimethylammonium) and poly(diallyldimethylammonium).

In one embodiment of the present invention, the heteropolyoxometalates are supported, in particular supported on oxides such as magnesium, aluminum, silicon, titanium or cerium oxide, preferably silicon oxide ($SiO_2$). The oxides, in particular the silicon oxide, preferably has a high surface area, e.g. at least about 150 m$^2$/g. The weight ratio of heteropolyoxometalates of the present invention to the supporting oxide, in particular silicon oxide, is about 10:1 to 1:100, preferably 1:1 to 1:10, e.g. about 1:2.

The heteropolyoxometalates of the formula (I), (II) and (III) can be prepared according to known processes.

One typical process for the preparation of the heteropolyoxometalates of the formula (I) and (II) comprises the steps of:
a) dissolving a salt comprising $[PZ_{11}O_{39}]^{7-}$ anions, when q=1,
a salt comprising $[PZ_{10}O_{36}]^{7-}$ anions, when q=2,
a salt comprising $[PZ_9O_{34}]^{9-}$ anions, when q=3, or
a salt comprising $[PO_4]^{3-}$ anions, optionally a salt comprising $VO_3^-$ anions, and a salt comprising $ZO_4^{2-}$ anions
wherein
Z is selected from Mo or W,
in an aqueous solvent, preferably water, to obtain a solution,
b) adding an acid in order to decrease the pH of the solution obtained after step a), and
c) adding a compound containing at least one cation selected from the group consisting of quaternary ammonium cations, quaternary phosphonium cations and tertiary sulfonium cations.

One typical process for the preparation of the heteropolyoxometalates of the formula (III) comprises the steps of:
a) dissolving a salt or acid comprising $[PZ_{12}O_{40}]^{3-}$, wherein Z is Mo or W in an aqueous solution of hydrogen peroxide, to obtain a solution,
b) adding an acid in order to decrease the pH of the solution of step a), and
c) adding a compound containing at least one cation selected from the group consisting of quaternary ammonium cations, quaternary phosphonium cations and tertiary sulfonium cations.

The heteropolyoxomolybdates or the heteropolyoxotungstates $[PZ_{9-11}O_{34-40}]^{y-}$, as used in step a) of the process for the preparation of the heteropolyoxometalates of the formula (I) and (II), and $[PZ_{12}O_{40}]^{3-}$, as used in step a) of for the preparation of the heteropolyoxometalates of the formula (III), can be obtained as known in the art, (e.g. as described in Holleman-Wiberg, Lehrbuch der Anorganischen Chemie, 101st edition, pages 1467-1469; M. T. Pope, Heteropoly and Isopoly Oxometalates, Springer, 1983; or Huheey et al., Anorganische Chemie, Prinzipien von Struktur and Reaktivität, 4. Auflage, 2012, chapter 16.2 etc). In particular, aqueous solutions comprising molybdate and tungstate anions as well as the corresponding heteroatom oxoanions or acids, i.e. phosphoric acid $H_3PO_4$, or the respective anion $PO_4^{3-}$, respectively, is acidified, and the heteropolyoxomolybdates or heteropolyoxotungstates are obtained by crystallization or chemical precipitation.

In step a) of the process for the preparation of the heteropolyoxometalates of the formula (I) $VO_3^-$ anions are provided in solution, and a corresponding salt comprising the lacunary (=vacant) heteropolyoxomolybdate or heteropolyoxotungstate anions $[PZ_{9-11}O_{34-39}]^{y-}$, wherein Z is Mo or W, or are added to obtain a solution in an aqueous solvent, preferably water.

In steps b) of the processes for the preparation of the heteropolyoxometalates of the formula (I), (II) or (III) a suitable acid, preferably a mineral acid, e.g. hydrochloric acid or sulfuric acid is added to decrease the pH of the solution obtained as a result of the steps a).

In steps c) of the processes for the preparation of the heteropolyoxometalates of the formula (I), (II) or (III) at least one compound containing a cation A as described above or a compound able to provide or release the cation A as described above is added. Preferably, the quaternary ammonium cation containing compound comprises a compound of formula (IV'), the quaternary phosphonium cation containing compound comprises a compound of formula (V') and the tertiary sulfonium cation containing compound comprises a compound of formula (VI')

$(R^1R^2R^3R^4N)_pX$      (IV'),

$(R^1R^2R^3R^4P)_pX$      (V'),

$(R^1R^2R^3S)_pX$      (VI')

wherein residues $R^1$, $R^2$, $R^3$ and $R^4$ are as defined above,
X is sulfate or a halogen ion, preferably chloride or bromide, and p is 2 if X is sulfate and p is 1 if X is a halogen ion. Preferably the quaternary ammonium cation containing compound to be used in the above processes comprises tetrabutylammonium bromide and/or tetrabutylammonium sulfate and/or tetrahexylammonium bromide, the quaternary phosphonium cation containing compound comprises tetrabutylphosphonium bromide and/or tetrabutylphoshonium sulfate and/or tetrahexylphosphonium bromide, and the tertiary sulfonium cation containing compound comprises tributylsulfonium bromide and/or tributylsulfonium sulfate and/or trihexylsulfonium bromide.

The heteropolyoxometalates of formula (I), (II) or (III) are obtained as a gel or precipitate, which is typically washed several times with $H_2O$ and may be dried to obtain a powder.

Optionally, the heteropolyoxometalate may be brought into any suitable shape by dissolving the gel or powder in a suitable organic solvent, e.g. ethanol, and drying the resulting solution to obtain a corresponding gel or powder. This way, heteropolyoxometalates may be mixed to prepare the heteropolyoxometalates comprising at least two different cations, in particular quaternary ammonium cations or at least two different heteropolxyoxometalate anions as described above.

Furthermore, it has been found that in the above described processes for the preparation of the heteropolyoxometalates used in the present invention intermediate compounds occur and can be isolated. These intermediate compounds are also heteropolyoxometalates, but they comprise an ion of the Formula (I'), (II') or (III')

$PV_qZ_{12-q}O_m$      (I'),

$P_2Z_{18}O_n$      (II'), or

$PZ_4O_o$      (III')

wherein
Z is selected from Mo or W,
q is 0, 1, 2 or 3,
m is a number above 20 and below 40,
n is a number above 31 and below 62,
o is a number above 12 and below 24,
and at least one cation A as defined above.

The charges of these ions depend on m, n and o, respectively, and are therefore not provided in the formulae. m, n and o designate any number within the above ranges and are not limited to integers. It is assumed that these ions are formed during the formation of the final heteropolyoxometalate anions which contain 40, 62 and 24 oxygen atoms, respectively. During this formation species occur and can be isolated which contain less oxygen atoms than the final anions. In preferred embodiments m is a number above 25, more preferably above 30, such as above 35, above 36, above 37, above 38 or above 39. In each case, m is below 40. n can be preferably above 36, more preferably above 41, such as above 46, above 51, above 56, above 57, above 58, above 59, above 60 and above 61. In any case, n is below 62. o can preferably be above 17, such as above 18, above 19, above 20, above 21, above 22 and above 23. In any case, o is below 24.

The heteropolyoxometalates of the Formula (I'), (II') and (III') as described above are useful in the preparation of a heteropolyoxometalate of the Formula (I), (II) and (III) as defined above. The heteropolyoxometalates of the Formula (I'), (II') and (III') can be converted into the final heteropolyoxometalate for example by stirring a suspension of these compounds in the presence of oxygen.

Furthermore, it has been found that also the intermediates of Formulae (I'), (II') and (III') exhibit the same antimicrobial and biocidal effects as the heteropolyoxometalates of the Formulae (I), (II) and (III). Therefore, also the intermediate compounds can be used for providing the desired properties to a surface of a substrate and are useful as component in surface layers, paints and coatings.

The present invention further relates to a substrate or a surface layer, paint or coating comprising a heteropolyoxometalate as described above. In one embodiment, the heteropolyoxometalate may be incorporated within a substrate or part of such substrate. The heteropolyoxometalate is incorporated into the substrate for example by mixing the ingredients from which the substrate is prepared before preparation of the substrate. For example, the substrate can be a natural or synthetic material, such as a plastic material, rubber, adhesive, sealant or silicon paste.

In order to provide a corresponding surface layer, the heteropolyoxometalates may be dissolved in a suitable solvent, preferably an organic solvent, e.g. ethanol and applied to the surface, followed by drying. Suitable excipients and advants as known for surface coatings may be added to the solution to be applied. Similarly, the heteropolyoxometalates may be added to paintings or coatings. Contrary to the known heteropolyoxometalates comprising cations such as $Li^+$, $Na^+$, $K^+$ or $NH_4^+$, the cations used in the present invention render the heteropolyoxometalates less soluble or even insoluble in water (at 20° C.). Preferably the solubility of the heteropolyoxometalates used in the present invention is below 1 mg/ml in water at 20° C., more preferably below 0.1 mg/ml water at 20° C., in particular below 0.01 mg/ml water at 20° C. This low solubility or even insolubility for aqueous liquids enables their use in particular in surface layers, paints or coatings which are in direct contact with liquids, typically aqueous liquids, to be stored or treated, in particular for disinfection.

The present invention relates to the use of the heteropolyoxometalates as described above for self-cleaning, stripping, disinfecting, self-sanitizing, biocidal, antimicrobial, and/or deodorizing purposes. Said purposes can be characterized by the ability to self-clean and/or strip by degrading, decomposing and stripping organic materials (e.g. oxidation of impurities such as grease, paint and other residues; avoiding formation of biofilms, etc.); by the ability to deter, render harmless, destroy and/or exert a controlling effect on all forms and/or parts of microbial life (e.g. bacteria, viruses, fungi, spore forms, etc.); and/or by the ability to remove and/or reduce offensive and/or unpleasant scents.

The above described qualities can be used to modify substrates. Wherein one or more parts (e.g. materials, additives, surface layers, inner layers, exterior, interior, etc.) of the said substrate comprise a heteropolyoxometalate as described above, and/or one or more of the surfaces (e.g. functional surfaces) of the said substrate are at least partially coated with surface layers, paints, coatings, cleaners and/or stripping agents, wherein said surface layers, paints, coatings, cleaners (e.g. oxidizing cleaners) and/or stripping agents comprise a heteropolyoxometalate. The substrates as described above can be selected from the group consisting of: containers for storage of drinking water (e.g. in the beverage industry), waste water, or surface water; containers for waste decomposition; containers for water purification; hospitals, medical equipment, slaughterhouses, ships, boats, roof coverings, roof tiles, indoor tiles, outdoor tiles, kitchen rooms, sinks, wash closets, toilets, portable toilets, ceramics, polymers, fibers, rain water sewers, exterior façades, elements of façades, pools, pumps, tubing, technical textiles, activewear fabrics, paper, wood, apparatus for air and water purification, apparatus for soil decontamination, window glass (e.g. self-cleaning windows), mirrors (e.g. anti-fog coatings for mirrors and/or glass), filter materials such as nonwovens, respirator masks, air filters, such as air-conditioner filters, water filters, and activated-carbon filters for water and/or air purification.

The heteropolyoxometalates may further be used for decomposition and/or degradation of organic materials (e.g. plastics, organic polymers, etc), such as for recycling, reuse, and/or disposal purposes.

The heteropolyoxometalates may further be used for pulp and/or fiber bleaching and/or treatment.

EXAMPLES

The following examples are intended to illustrate the invention but should not be construed as limiting.

Example 1

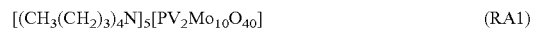

$[(CH_3(CH_2)_3)_4N]_5[PV_2Mo_{10}O_{40}]$ (RA1)

Abbreviation: (TBA-$PV_2Mo_{10}$+$SiO_2$)

24.4 g $NaVO_3$+100 mL boiling $H_2O$ added to 7.1 g $Na_2HPO_4$+100 mL $H_2O$, then cooled to RT after that 5 mL conc. $H_2SO_4$ was added, then 121 g $Na_2MoO_4 \times 2H_2O$ in 200 mL $H_2O$ are added and stirred vigorously, then 85 mL conc. $H_2SO_4$ are slowly added, to half of the obtained homogeneous solution 19.5 g of TBA-Br was added to obtain orange $TBA_5[PMo_{10}V_2O_{40}]$, which was thoroughly washed with water, the obtained powder was dissolved in minimum amount of acetone and 10 g of $SiO_2$ was added to the solution. The resulting mixture was stirred vigorously and transferred by layering on the Petri dish, and air-dried for 24 hours.

Weight of the substance: 27 g
Molecular Weight: 158.8 g/mol
Number of moles: 170 mmoles Example 2

$[(CH_3(CH_2)_3)_4N]_3[PW_4O_{24}]$ (RA3)

Abbreviation: (TBA-$PW_4$+$SiO_2$)

10 g $H_3PW_{12}O_{40}$ in 70 mL 30% $H_2O_2$ was added 10 mL $H_3PO_4$. The solution was stirred for 4 h at 40° C., to the obtained homogeneous solution 12 g of TBA-$SO_4$ was added to obtain white $TBA_3[PW_4O_{24}]$, which was thoroughly washed with water, the obtained powder was dissolved in minimum amount of acetone and 10 g of $SiO_2$ was added to the solution. The resulting mixture was stirred vigorously and transferred by layering on the Petri dish, and air-dried for 24 hours.

Weight of the substance: 27 g
Molecular Weight: 158.4 g/mol
Number of moles: 170 mmoles Example 3

$[(CH_3(CH_2)_5)_4N]_3[PW_4O_{24}]$ (RA4)

Abbreviation: (THA-$PW_4$+$SiO_2$)

10 g $H_3PW_{12}O_{40}$ in 70 mL 30% $H_2O_2$ was added 10 mL $H_3PO_4$. The solution was stirred for 4 h at 40° C., to the obtained homogeneous solution 12 g of THA-Cl was added to obtain white $THA_3[PW_4O_{24}]$, which was thoroughly washed with water, the obtained powder was dissolved in minimum amount of acetone and 10 g of $SiO_2$ was added to the solution. The resulting mixture was stirred vigorously and transferred by layering on the Petri dish, and air-dried for 24 hours.

Weight of the substance: 27 g
Molecular Weight: 158.7 g/mol
Number of moles: 170 mmoles

Example 4

[(CH$_3$(CH$_2$)$_3$)$_3$P((CH$_2$)$_{13}$CH$_3$)]$_3$[PW$_4$O$_{24}$]

Phosphotungstic acid (10 g, 3.47 mmol) was dissolved in 70 ml of 30% H$_2$O$_2$. 10 ml of 5M H$_3$PO$_4$ was added and the solution was stirred for 4 h at 40° C. The reaction mixture was then cooled to room temperature. (Reaction mixture A)

Since the exact molar ratio of [PW$_4$O$_{24}$]$^{3-}$ to the cation was unknown, 10 g of it were assumed as a product. Therefore, 3 equivalents of cations TBTDP$^+$ (tributyltetradecylphosphonium) were added as solid chloride to a reaction mixture A and stirred for 8-10 min. The solution was decanted and the precipitates were washed thoroughly with double deionized water. The Cl$^-$ contents (i.e. unreacted cation) was checked by AgNO$_3$.

The precipitates (as gel) was dissolved in acetone and poured into a petridish.

Comparative Example 1

[(CH$_3$(CH$_2$)$_5$)$_4$N]$_7$SiV$_3$W$_9$O$_{40}$: SiO$_2$ (MS3)

Abbreviation: (THA-SiV$_3$W$_9$+SiO$_2$)

NaVO$_3$ (0.7 g, 6.0 mmol) and 5.0 g of Na$_{10}$[α-SiW$_9$O$_{34}$]*xH$_2$O (2.0 mmol) were mixed as dry powders and added to 50 ml of H$_2$O at room temperature. The solution was stirred vigorously during 30 min and then 6 M HCl was added dropwise to bring the pH to 1.5, and a clear wine red solution developed. The resulting solution was filtered and 15.0 g of tetrahexylammonium bromide (THABr) was added. The orange gel was separated by removing the upper aqueous layer and thoroughly washed with H$_2$O.

(THA-SiV$_3$W$_9$+SiO$_2$)

The obtained powder of THA-SiV$_3$W$_9$ was dissolved in minimum amount of ethanol and 10 g of SiO$_2$ (washed and calcined, p. a., granulation 0.1-0.5 mm min. 70%, CAS no. 14808-60-7, Sigma-aldrich) was added to the solution. The resulting mixture was stirred vigorously and transferred to the Petri dish, air-dried for 24 hours and then dried in the oven for 12 hours at 55° C.

Weight of the substance: 29.8 g
Molecular Weight: 175.3 g/mol
Number of moles: 174 mmoles

Example 5

The heteropolyoxometalates of Examples 1 to 3 and of Comparative Example 1 were tested for their disinfection affectivity. Laundry waste water obtained from a domestic washing machine was tested for its total aerobic bacterial count before storage and after storage for 100 minutes and 5 days in a Petri dish covered with the respective heteropolyoxometalate. The results are summarized in the following table:

| total aerobic bacterial count | t = 0 | t = 100 min | t = 5 days |
|---|---|---|---|
| blank value | 1.3E+06 | 9.9E+05 | 6.5E+07 |
| Example 1 | 1.3E+06 | 8.5E+05 | 300 |
| Example 2 | 1.3E+06 | 1.5E+05 | 100 |
| Example 3 | 1.3E+06 | 1.1E+05 | <100 |

| total aerobic bacterial count | t = 0 | t = 100 min | t = 5 days |
|---|---|---|---|
| Example 4 | 1.4E+06 | 2100 | 0 |
| Comparative Example 1 | 6.6E+05 | 1.4E+06 | 1.6E+06 |

These results show that the heteropolyoxometalates of the Examples 1, 2, 3 and 4 show an excellent disinfecting efficiency, while the heteropolyoxometalates of Comparative Example 1, which is based on silicon, did not show antimicrobial activity.

Example 6

The thermal stability of the heteropolyoxometalates of Examples 3 and 4 was determined by TGA (thermogravimetric analysis) and DSC (differential scanning calorimetry).

Figure 2:
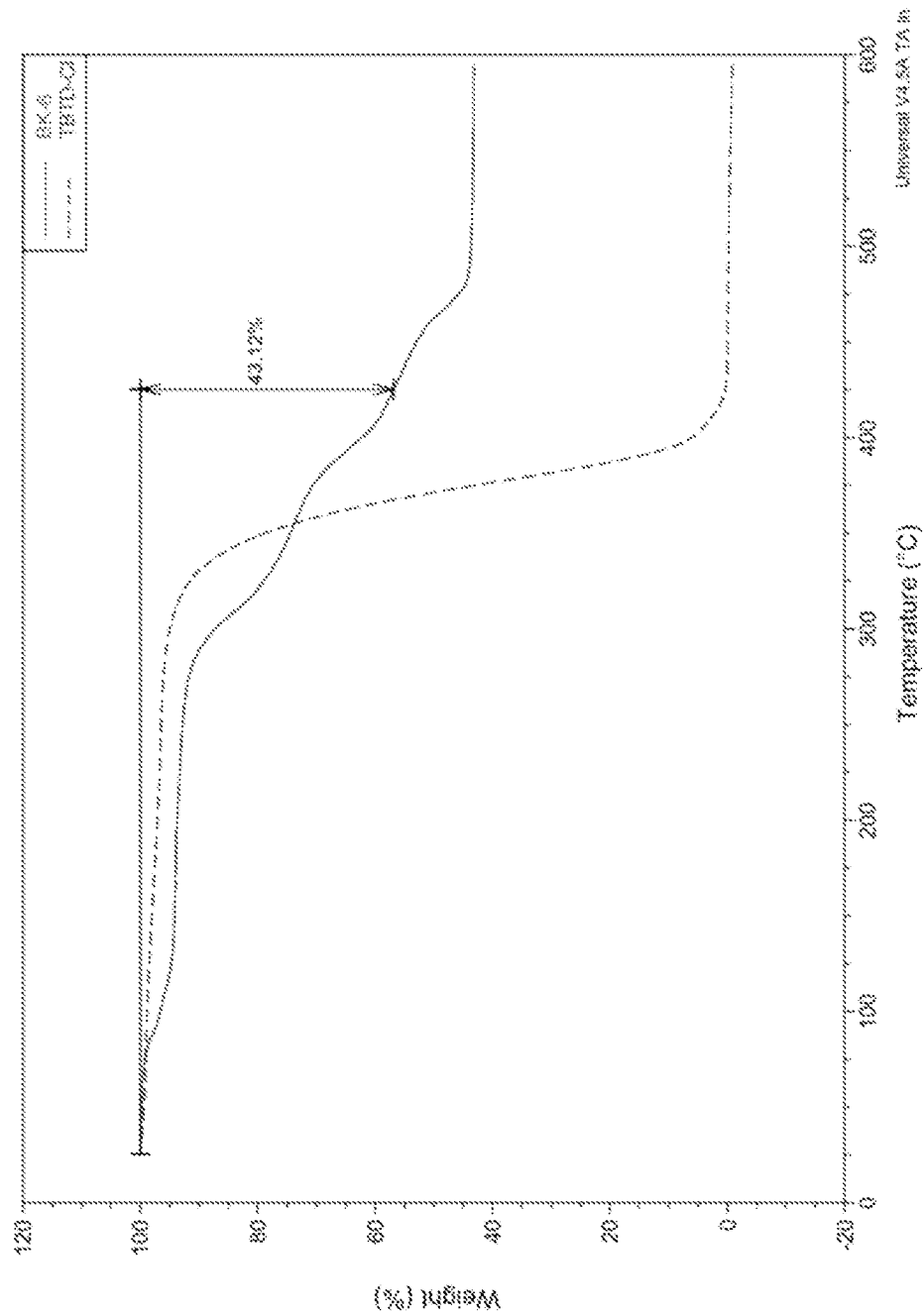
FIG. 2 shows the TGA/DSC measurement results of the heteropolyoxometalate of Example 4.

The results of these measurements are shown in FIG. 1 for Example 3 and in FIG. 2 for Example 4. RA4 and BK-6 designate the respective heteropolyoxometalates, THA designates tetrahexylammonium chloride and TBTD designates tributyltetradecylphosphonium chloride.

The data show that the compound of Example 3 is thermally stable up to about 140° C. Surprisingly, it was found that the analogous phosphonium compound of Example 4 exhibited a thermal stability of up to about 300° C.

The invention claimed is:

1. A method for making a functional surface, the method comprising:
   forming a gel or a powder with at least one heteropolyoxometalate selected from the following (I), (II), and/or (III) Formulas:

$$A_{q+3}PV_qZ_{12-q}O_{40} \quad (I),$$

$$A_6P_2Z_{18}O_{62} \quad (II), \text{ and/or}$$

$$A_3PZ_4O_{24} \quad (III);$$

wherein
   Z is selected from Mo or W;
   q is 0, 1, 2 or 3; and
   A is selected from one or more cations and comprises at least one cation selected from the group consisting of quaternary ammonium cations, quaternary phosphonium cations, and tertiary sulfonium cations;
   dissolving the gel or powder into a coating material;
   contacting the coating material to a substrate;
   drying the coating material to form the functional surface;
   wherein the functional surface includes self-cleaning, disinfecting, self-sanitizing, biocidal, antimicrobial, and/or deodorizing properties.

2. The method according to claim 1, wherein the heteropolyoxometalate has the Formula (I) and Z is Mo and q=2.

3. The method according to claim 1, wherein Z in the heteropolyoxometalate is Mo.

4. The method according to claim 1, wherein the heteropolyoxometalate has the Formula (III) and Z is W.

5. The method according to claim 1, wherein Z in the heteropolyoxometalate is W.

6. The method according to claim 1, wherein A is selected from quaternary ammonium cations and quaternary phosphonium cations, and wherein A comprises at least one of each of these two different cations.

7. The method according to claim 1, wherein A comprises at least one quaternary ammonium cation.

8. The method according to claim 7, wherein A comprises at least two different quaternary ammonium cations.

9. The method according to claim 1, wherein the quaternary ammonium cation has the Formula (IV), the quaternary phosphonium cation has the Formula (V), and the tertiary sulfonium cation has the Formula (VI):

$$R^1R^2R^3R^4N^+ \quad (IV),$$

$$R^1R^2R^3R^4P^+ \quad (V),$$

$$R^1R^2R^3S^+ \quad (VI);$$

wherein residues $R^1$, $R^2$, $R^3$, and $R^4$ are independently selected from polymers and $C_1$ to $C_{20}$ hydrocarbons, and optionally at least two of the residues $R^1$, $R^2$, $R^3$ and, if present, $R^4$ are part of a ring or form a ring together with the nitrogen, phosphor or sulfur atom.

10. The method according to claim 1, wherein A comprises a tetrabutylammonium cation, a tetrahexylammonium cation, a tetraoctylammonium cation, a methyltrioctylammonium cation, a tributyltetradecylammonium cation, a tetrabutylphosphonium cation, a tetrahexylphosphonium cation, a tetraoctylphosphonium cation, a methyltrioctylphosphonium cation and/or a tributyltetradecylphosphonium cation.

11. The method according to claim 1, wherein the heteropolyoxometalate is selected from the group consisting of $[(CH_3(CH_2)_5)_4N]_3[PW_4O_{24}]$, $[(CH_3(CH_2)_7)_4N]_3[PW_4O_{24}]$, $[(CH_3(CH_2)_7)_3N(CH_3)]_3[PW_4O_{24}]$ and $[(CH_3(CH_2)_3)_3P((CH_2)_{13}CH_3)]_3[PW_4O_{24}]$.

12. The method according to claim 1, wherein the heteropolyoxometalate is selected from the group consisting of $[(CH_3(CH_2)_5)_4N]_3[PW_4O_{24}]$, $[(CH_3(CH_2)_7)_4N]_3[PW_4O_{24}]$ and $[(CH_3(CH_2)_3)_3P((CH_2)_{13}CH_3)]_3[PW_4O_{24}]$.

* * * * *